(12) United States Patent
Mo et al.

(10) Patent No.: US 9,035,084 B2
(45) Date of Patent: May 19, 2015

(54) PREPARATION METHOD OF AROMATIC BORONATE COMPOUNDS

(75) Inventors: Fanyang Mo, Beijing (CN); Yubo Jiang, Beijing (CN); Di Qiu, Beijing (CN); Wengang Yao, Beijing (CN); Yan Zhang, Beijing (CN); Jianbo Wang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 156 days.

(21) Appl. No.: 13/497,591

(22) PCT Filed: Aug. 27, 2010

(86) PCT No.: PCT/CN2010/001301
§ 371 (c)(1),
(2), (4) Date: Mar. 22, 2012

(87) PCT Pub. No.: WO2011/035532
PCT Pub. Date: Mar. 31, 2011

(65) Prior Publication Data
US 2012/0184768 A1    Jul. 19, 2012

(30) Foreign Application Priority Data
Sep. 25, 2009    (CN) .......................... 2009 1 0093548

(51) Int. Cl.
C07F 5/04    (2006.01)
C07F 5/02    (2006.01)

(52) U.S. Cl.
CPC ...................... C07F 5/025 (2013.01)

(58) Field of Classification Search
USPC ........................................ 558/286
See application file for complete search history.

(56) References Cited

U.S. PATENT DOCUMENTS 6,559,310 B2    5/2003    Marcuccio et al.
7,612,218 B2    11/2009    Miyaura et al.

FOREIGN PATENT DOCUMENTS

CN        102030770        4/2011
GB        WO 02/38568    *    5/2002    ................... 558/288
WO        WO 2009/126691    *    10/2009    ................... 558/288

OTHER PUBLICATIONS

International Search Report for PCT/CN2010/001301 mailed on Dec. 9, 2010.
International Search Report for PCT/CN2010/001301 mailed on Jan. 30, 2013.
Fanyang Mo, et al.; Direct Conversion of Arylamines to Pnacol Boronates: A Metal-Free Borylation Process; Angewandte Chemie International Edition; Feb. 1, 2010; pp. 1846-1849; vol. 49, No. 10.
A. S. R. Jennings, et al; Imidazo [1,2-b] [1,2,4] triazines as alpha2/alpha3 subtype selective GABAA agonists for the treatment of anixety; Bioorganic & Medicinal Chemistry Letters, Pergamon, Elsevier Science, GB; Mar. 15, 2006; pp. 1477-1480; vol. 16, No. 6.

* cited by examiner

*Primary Examiner* — Samantha Shterengarts
(74) *Attorney, Agent, or Firm* — Amin, Turocy & Watson, LLP

(57) ABSTRACT

Preparation method of aromatic boronate compound is provided, in which the is as follows: reacting aromatic amine Ar-NH$_2$, with diboronic ester and alkyl nitrite in the presence of organic solvent, where Ar represents non-heterocyclic aryl. It enables for the first time the preparation of aromatic boronate from aromatic amine in one step by the present method.

10 Claims, No Drawings

PREPARATION METHOD OF AROMATIC BORONATE COMPOUNDS

TECHNICAL FIELD

The invention belongs to the field of organic synthesis, and specifically relates to a preparation method for aromatic boronate compound.

BACKGROUND ART

Aromatic boronates are important industrial chemicals, which are widely used in scientific researches and industrial productions. In scientific researches, aromatic boronates are mainly applied in organic synthesis. Aromatic boronates are commonly used as molecular building blocks and involved in various organic reactions to construct much complicated target compounds. In industrial production, aromatic boronates are mainly applied for the preparation of materials, pharmaceuticals and pesticides. The synthetic methods for aromatic boronates have been developed and improved over the years. Among known synthetic methods, most of aromatic boronates are synthesized through the following established procedures: 1) aromatic boronate is obtained by preparing a corresponding Grignard reagent or lithium reagent from an aromatic halide and then reacting with a borate; 2) aromatic boronate is obtained by reacting an aromatic iodide or bromide with a diboronic ester under the catalysis of palladium. The drawbacks of these methods are as follows: 1) both of them start from aromatic halides, which are not readily available; 2) metal reagents are used as the starting material or the catalyst, which results in the formation of side-products, and take the first method for instance, the aryl Grignard reagent or lithium reagent may further attack newly formed product, the aromatic boronate, to yield diaryl borinate or triaryl borane; 3) both of them are not environment-friendly and need complicated operations, harsh conditions and rigorously anhydrous and oxygen-free environments, the first method needs to be performed at low temperature while the second method needs to be performed at high temperature; 4) both of them result in high costs because palladium catalyst is expensive and the cost for preparing aromatic halide is higher than the corresponding aromatic amine.

DISCLOSURE OF THE INVENTION

The object of the invention is to provide a highly efficient and air tolerable preparation method for aromatic boronates. Wide ranges of substrates are compatible in this method. Thus, a series of aromatic boronates having various substituents can be synthesized through this method.

The technical solutions of the invention are described as follows.

The invention relates to a preparation method for aromatic boronate, wherein the aromatic boronate (Ar-Bpin) is obtained by a reaction of an aromatic amine (Ar-NH$_2$), a diboronic ester and an alkyl nitrite in an organic solvent.

The aryl group (Ar-) of aromatic amine is a non-heterocyclic aryl, which can be substituted or unsubstituted aryl group (for example, substituted or unsubstituted phenyl).

Different functional groups are well tolerated to the method of the invention. The aryl group of the aromatic amine can bear one or more substituents in addition to amino group. The substitutions on the meta or para-positions are preferred, while the ortho-substituted substrates result in relatively lower yields. The substituents are not limited by any means. Common substituents include, such as alkyl, alkoxy, amide, ester, keto carbonyl, nitro, halogen and the like. The aryl group can bear one or more of these substituents. When bearing more substituents, said substituents can be the same or different, and the adjacent two substituents can be independent or can form a ring.

Above alkyl group is preferably alkyl having 1 to 10 carbon atoms, such as methyl, ethyl, propyl, iso-propyl, n-butyl, iso-butyl, tert-butyl, sec-butyl, amyl, neoamyl and the like, more preferably alkyl having 1 to 4 carbon atoms, and even more preferably methyl, ethyl and propyl.

Above alkoxy group is preferably alkoxy having 1 to 10 carbon atoms, such as methoxy, ethoxy, propoxy, iso-propoxy, butoxy, iso-butoxy, tert-butoxy, sec-butoxy and the like, more preferably alkoxy having 1 to 4 carbon atoms, and even more preferably methoxy, ethoxy and iso-propoxy.

Above amide group is preferably acetamido, propionamido, butyramido and the like.

Above ester group is preferably methyl formate, ethyl formate, propyl formate, butyl formate and the like.

Above keto carbonyl group is preferably acetyl, propionyl, butyryl and the like.

Above halogen is fluorine, chlorine, bromine or iodine.

In the method of the invention, the diboronic ester is preferably bis(pinacolato)diboron.

In the method of the invention, the alkyl group of the alkyl nitrite is generally linear or branched alkyl having 3 to 6 carbon atoms, preferably alkyl having 4 to 5 carbon atoms, such as iso-amyl or tert-butyl, and more preferably tert-butyl.

When the diboronic ester is bis(pinacolato)diboron, the method of the invention can be represented by the following reaction:

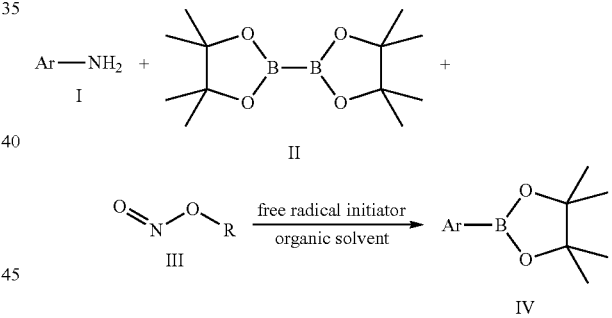

In the reaction, compound I represents aromatic amine, compound II is bis(pinacolato)diboron, compound III represents alkyl nitrite (wherein R represents alkyl), compound IV represents the product, aromatic boronate.

In the method of the invention, the reaction is preferably promoted by a free radical initiator. Commercially available free radical initiators such as benzoyl peroxide and azodiisobutyronitrile can be used without special treatment. Its amount is preferably 2-10 mol % based on the amount of aromatic amine. It should be noted that the reaction can also take place without addition of free radical initiator. However, the yield can be increased and the reaction time can be reduced with the addition of free radical initiator.

The organic solvent used in the method of the invention is one selected from the group consisting of dichloromethane, 1,2-dichloroethane, ethyl acetate and acetonitrile. Commercially available organic solvent can be used without special treatment. The amount of the solvent is preferably 2 to 3 mL per mmol of aromatic amine.

The preferred molar ratio of three reactants, i.e., aromatic amine: diboronic ester: alkyl nitrite, in the method of the invention ranges from 1:1:1.5 to 1:1.2:1.5.

The reaction temperature and time are changed depending on different starting materials. The reaction is completed until no bubble produced from the reaction system. The reaction temperature generally ranges from room temperature to 60° C.; the reaction time generally ranges from 0.5 to 4 hours. Oil-bath (such as silicon oil, paraffin oil or the like) or other heating means can be employed for heating process.

Workup operations to the reaction product, including concentration and purification, are preferred after the completion of the reaction.

The concentration process can employ methods such as distillation under normal pressure or reduced pressure. For example, a rotary evaporator can be used for vacuum evaporation.

The purification process can provide pure product through column chromatography.

The method of the invention enables, for the first time, a one-step conversion from aromatic amine to aromatic boronate with higher efficiency and lower cost. This method can be widely applied in the synthesis of aromatic boronates. The present invention has the following advantages as compared with the prior art.

1. The main starting material involved in the invention is aromatic amine. This is an important complement to the existing method, which employs aromatic halide as starting material. The cost for preparing aromatic amine is lower than the corresponding aromatic halide. Some aromatic halides are prepared by employing the corresponding aryl amines as starting materials (such as via Sandmeyer reaction).

2. The reaction involved in the method of the invention can be readily performed under air, without the need of rigorously anhydrous and oxygen-free conditions, and thus can be operated conveniently and easily.

3. The reaction involved in the method of the invention is well tolerated and applicable to different functional groups. The substituents on the aryl group can be alkyl, alkoxy, ester, amide, keto carbonyl, nitro, halogens (F, Cl, Br and I) and the like.

DETAILED DESCRIPTION OF THE INVENTION

The present invention will be described in more details by means of examples. However, the scope of the present invention is not limited to these examples.

EXAMPLE 1

Synthesis of 2-(4-methoxyphenyl)-4,4,5,5-tetramethyl-1,3,2-dioxaborolane

Bis(pinacolato)diboron $B_2pin_2$ (1.2 mmol, 305 mg), benzoyl peroxide (0.1 mmol, 24 mg), 4-$MeOC_6H_4NH_2$ (1 mmol, 123 mg) and acetonitrile (3 mL) were added to a 25 mL tube-type reactor, followed by the addition of tert-butyl nitrite (1.5 mmol, 154 mg). The reaction was conducted at room temperature for 4 h. The solution was concentrated after the reaction and the resultant was purified by column chromatography (eluted by petroleum ether) to give 2-(4-methoxyphenyl)-4,4,5,5-tetramethyl-1,3,2-dioxaborolane having the following structure:

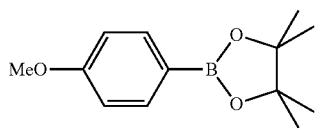 [SMILES: COc1ccc(B2OC(C)(C)C(C)(C)O2)cc1]

This compound is colorless liquid and obtained in 72% yield. Its NMR data are as follows: $^1H$ NMR (400 MHz, $CDCl_3$) δ 7.75 (d, 1H, J=8.7 Hz), 6.89 (d, 1H, J=8.7 Hz), 3.82(s, 3H), 1.33(s, 12H); $^{13}C$ NMR (100 MHz, $CDCl_3$) δ 162.1, 136.4, 113.2, 83.5, 55.0, 24.8.

EXAMPLE 2

Synthesis of 4,4,5,5-tetramethyl-2-(3-(trifluoromethyl)phenyl)-1,3,2-dioxaborolane $B_2pin_2$ (1.0 mmol, 254 mg), benzoyl peroxide (0.02 mmol, 5 mg), 3-$F_3CC_6H_4NH_2$ (1 mmol, 161 mg) and acetonitrile (3 mL) were added to a 25 mL tube-type reactor, followed by the addition of tert-butyl nitrite (1.5 mmol, 154 mg). The reaction was conducted at room temperature for 4 h. The solution was concentrated after the reaction and the resultant was purified by column chromatography (eluted by petroleum ether:ethyl acetate=30:1, V:V) to give 4,4,5,5-tetramethyl-2-(3-(trifluoromethyl)phenyl)-1,3,2-dioxaborolane having the following structure:

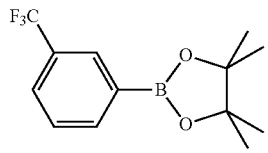 [SMILES: CC1(C)OB(c2cccc(C(F)(F)F)c2)OC1(C)C]

This compound is colorless liquid and obtained in 70% yield. Its NMR data are as follows: $^1NNMR$ (400 MHz, $CDCl_3$) δ 8.09~8.06(m, 1H), 7.97 (d, 1H, J=7.4 Hz), 7.70 (d, 1H, J=7.9 Hz), 7.48 (t, 1H, J=7.7 Hz), 1.36(s, 12H); $^{13}C$ NMR (100 MHz, $CDCl_3$) δ 137.9, 131.4, 131.3, 131.3, 131.2, 130.2, 129.8, 129.8, 128.8, 128.0, 127.8, 127.7, 127.7, 127.7, 125.6, 122.9, 84.2, 24.8.

EXAMPLE 3

Synthesis of 1-(4-(4,4,5,5-tetramethyl-1,3,2-dioxaborolan-2-yl)phenyl)ethanone $B_2pin_2$ (1 mmol, 254 mg), benzoyl peroxide (0.02 mmol, 5 mg), 1-(4-aminophenyl)ethanone (1 mmol, 135 mg) and acetonitrile (3 mL) were added to a 25 mL tube-type reactor, followed by the addition of tert-butyl nitrite (1.5 mmol, 154 mg). The reaction was conducted at room temperature for 4 h. The solution was concentrated after the reaction and the resultant was purified by column chromatography (eluted by petroleum ether:ethyl acetate=20:1, V:V) to give 1-(4-(4,4,5,5-tetramethyl-1,3,2-dioxaborolan-2-yl)phenyl)ethanone having the following structure:

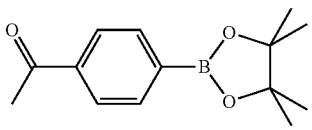 [SMILES: CC(=O)c1ccc(B2OC(C)(C)C(C)(C)O2)cc1]

This compound is pale yellow solid and obtained in 60% yield. Its NMR data are as follows: $^1$H NMR (400 MHz, CDCl$_3$) δ 7.94~7.88 (m, 4H), 2.62 (s, 3H), 1.36 (s, 12H); $^{13}$C NMR (100 MHz, CDCl$_3$) δ 198.4, 138.9, 134.8, 127.2, 105.3, 84.1, 26.7, 24.8.

EXAMPLE 4

Synthesis of ethyl 4-(4,4,5,5-tetramethyl-1,3,2-dioxaborolan-2-yl)benzoate

B$_2$pin$_2$ (1.0 mmol, 254 mg), benzoyl peroxide (0.02 mmol, 5 mg), ethyl 4-aminobenzoate (1 mmol, 165 mg) and acetonitrile (3 mL) were added in a 25 mL tube-type reactor, followed by the addition of tert-butyl nitrite (1.5 mmol, 154 mg). The reaction was conducted at room temperature for 4 h. The solution was concentrated after the reaction and the resultant was purified by column chromatography (eluted by petroleum ether:ethyl acetate=20:1, V:V) to give ethyl 4-(4,4,5,5-tetramethyl-1,3,2-dioxaborolan-2-yl)benzoate having the following structure:

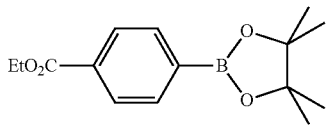 [SMILES: CCOC(=O)c1ccc(B2OC(C)(C)C(C)(C)O2)cc1]

This compound is pale yellow liquid and obtained in 79% yield. Its NMR data are as follows: $^1$H NMR (400 MHz, CDCl$_3$) δ 8.02 (d, 2H, J=8.4 Hz), 7.87 (d, 2H, J=8.4 Hz), 4.38 (q, 1H, J=7.1 Hz), 1.42~1.35(m, 15H); $^{13}$C NMR (100 MHz, CDCl$_3$) δ 166.6, 134.5, 132.6, 128.5, 84.1, 61.0, 24.8, 14.2.

EXAMPLE 5

Synthesis of 2-(3,4-dichlorophenyl)-4,4,5,5-tetramethyl-1,3,2-dioxaborolane

B$_2$pin$_2$ (1.0 mmol, 305 mg), benzoyl peroxide (0.02 mmol, 5 mg), 3,4-dichloroaniline (1 mmol, 161 mg) and acetonitrile (3 mL) were added in a 25 mL tube-type reactor, followed by the addition of tert-butyl nitrite (1.5 mmol, 154 mg). The reaction was conducted at room temperature for 4 h. The solution was concentrated after the reaction and the resultant was purified by column chromatography (eluted by petroleum ether:ethyl acetate=20:1, V:V) to give 2-(3,4-dichlorophenyl)-4,4,5,5-tetramethyl-1,3,2-dioxaborolane having the following structure:

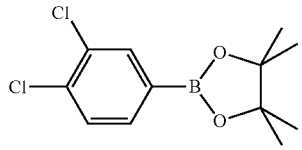

This compound is colorless liquid and obtained in 54% yield. Its NMR data are as follows: $^1$H NMR (400 MHz, CDCl$_3$) δ 7.86 (d, 1H, J=1.4 Hz), 7.60 (dd, 1H, J$_1$=1.4 Hz, J$_2$=7.9 Hz), 7.43 (d, 1H, J=7.9 Hz), 1.34(s, 12H); $^{13}$C NMR (100 MHz, CDCl$_3$) δ 136.5, 135.4, 133.7, 132.2, 129.9, 84.3, 24.8.

EXAMPLE 6

Synthesis of N-(4-(4,4,5,5-tetramethyl-1,3,2-dioxaborolan-2-yl)phenyl)acetamide

B$_2$pin$_2$ (1.2 mmol, 305 mg), benzoyl peroxide (0.02 mmol, 5 mg), N-(4-aminophenyl)acetamide (1 mmol, 150 mg) and acetonitrile (3 mL) were added in a 25 mL tube-type reactor, followed by the addition of tert-butyl nitrite (1.5 mmol, 154 mg). The reaction was conducted at room temperature for 1 h. The solution was concentrated after the reaction and the resultant was purified by column chromatography (eluted by petroleum ether:ethyl acetate=20:1, V:V) to give N-(4-(4,4,5,5-tetramethyl-1,3,2-dioxaborolan-2-yl)phenyl)acetamide having the following structure:

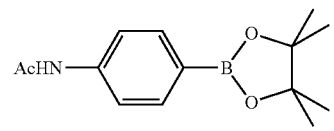

This compound is white solid and obtained in 93% yield. Its NMR data are as follows: $^1$H NMR (400 MHz, CDCl$_3$) δ 7.76 (d, 1H, J=8.4 Hz), 7.53 (d, 1H, J=8.3 Hz), 2.16(s, 3H), 1.33~1.24(m, 12H); $^{13}$C NMR (100 MHz, CDCl$_3$) δ 168.5, 140.5, 135.6, 128.8, 119.9, 118.5, 83.6, 74.9, 24.9, 24.7, 24.5, 24.4.

What is claimed is:

1. A method for preparing an aromatic boronate, consisting of charging a reaction vessel with an aromatic amine Ar-NH$_2$, a diboronic ester and an alkyl nitrite in an organic solvent, wherein the aryl group Ar of the aromatic amine is non-heterocyclic, the aromatic boronate being obtained in a one-step conversion reaction.

2. The method of claim 1, wherein the aryl group Ar has one or more substituents.

3. The method of claim 2, wherein the substituents are the same or different and selected from the group consisting of alkyl, alkoxy, amide, ester, keto carbonyl, nitro and halogens, and where two adjacent substituents can be independent or can form a ring.

4. The method of claim 1, wherein the diboronic ester is bis(pinacolato)diboron.

5. The method of claim 1, wherein the alkyl group of the alkyl nitrite is a linear or branched alkyl having 3 to 6 carbon atoms.

6. The method of claim 1, wherein the organic solvent is selected from the group consisting of dichloromethane, 1,2-dichloroethane, ethyl acetate and acetonitrile.

7. The method of claim 1, wherein a free radical initiator is added to promote the reaction.

8. The method of claim 7, wherein the free radical initiator is benzoyl peroxide or azodiisobutyronitrile.

9. The method of claim 7, wherein the amount of the free radical initiator is 2-10 mol % based on the amount of the aromatic amine.

10. The method of claim 1, wherein the molar ratio of aromatic amine : diboronic ester : alkyl nitrite ranges from 1:1:1.5 to 1:1.2:1.5.

* * * * *